United States Patent
Fredriksson et al.

(10) Patent No.: US 10,888,712 B2
(45) Date of Patent: Jan. 12, 2021

(54) METHOD, A COMPUTER PROGRAM PRODUCT AND A SYSTEM FOR OPTIMIZATION OF RADIOTHERAPY TREATMENT PLANNING

(71) Applicant: RaySearch Laboratories AB, Stockholm (SE)

(72) Inventors: Albin Fredriksson, Stockholm (SE); Erik Engwall, Hägersten (SE)

(73) Assignee: RaySearch Laboratories AB, Stockholm (SE)

( * ) Notice: Subject to any disclaimer, the term of this patent is extended or adjusted under 35 U.S.C. 154(b) by 478 days.

(21) Appl. No.: 15/567,400

(22) PCT Filed: Apr. 11, 2016

(86) PCT No.: PCT/EP2016/057921
§ 371 (c)(1),
(2) Date: Oct. 18, 2017

(87) PCT Pub. No.: WO2016/166059
PCT Pub. Date: Oct. 20, 2016

(65) Prior Publication Data
US 2018/0289980 A1   Oct. 11, 2018

(30) Foreign Application Priority Data

Apr. 14, 2015   (EP) .................................. 15163564

(51) Int. Cl.
*A61N 5/10* (2006.01)

(52) U.S. Cl.
CPC ......... *A61N 5/1037* (2013.01); *A61N 5/1031* (2013.01); *A61N 5/1038* (2013.01)

(58) Field of Classification Search
CPC ... A61N 5/1037; A61N 5/1038; A61N 5/1031
See application file for complete search history.

(56) References Cited

FOREIGN PATENT DOCUMENTS

| WO | WO-2006/130771 A2 | 12/2006 |
| WO | WO-2010/043340 A1 | 4/2010 |

OTHER PUBLICATIONS

A. Fredriksson et al., "Optimizing the Scenario Positions for Robust Radiation Therapy Treatment Planning", URL:https://people.kth.se/~andersf/doc/scenariooptimization.pdf, Oct. 10, 2012, p. 1-p. 21.
E. Heath et al., "Incorporating Uncertainties in Respiratory Motion Into 4D Treatment Plan Optimization", Medical Physics 36, (2009), pp. 3059-3071, doi 10.1118/1.3148582, p. 3059-p. 3071.

*Primary Examiner* — Kaylee R Wilson
(74) *Attorney, Agent, or Firm* — Faegre Drinker Biddle & Reath LLP

(57) ABSTRACT

An optimization method for a radiotherapy plan using robust optimization to handle different scenarios that may occur during one treatment session because of patient movement. The optimization is based on the period and amplitude of the movement, the starting point of the treatment session within a period and the delivery time structure.

16 Claims, 2 Drawing Sheets

METHOD, A COMPUTER PROGRAM PRODUCT AND A SYSTEM FOR OPTIMIZATION OF RADIOTHERAPY TREATMENT PLANNING

This application is the National Stage of International Application No. PCT/EP2016/057921, filed Apr. 11, 2016, and claims benefit of European Patent Application No. 15163564.6 filed Apr. 14, 2015.

TECHNICAL FIELD

The present invention relates to the field of radiotherapy, and in particular to the compensation for patient movement during a radiotherapy session.

BACKGROUND AND RELATED ART

Radiotherapy involves subjecting a target, such as a tumour, within a patient to one or more radiation beams. Ideally, a specific dose should be delivered to the target and minimal radiation should reach the surrounding tissue. In particular, the radiation to critical tissues or organs, such as the heart, should be minimized. The maximum and minimum doses for various tissues and organs are specified in a set of clinical goals. Normally the radiotherapy treatment is distributed in a number of sessions, or fractions, for example once a day for a number of days or weeks. A fraction is normally delivered over a period of a few minutes.

Adaptive radiotherapy methods have been developed for taking into account the changes that occur to the patient's body between the fractions, for example tumour shrinkage or motion. After each fraction, or after a number of fractions, the treatment plan may be re-optimized in response to actual accumulated dose and/or changes in, for example, the patient's anatomy. However, it is not unusual that the patient's body moves during a fraction in such a way that the target is displaced continuously relative to the beam. In particular, if the tumour is located in the lungs, the patient's breathing cycle will cause the tumour to move up and down, and possibly sideways, several times during a fraction, while the beam will be aimed relative to a fix reference position. Cyclic movements may also occur in other organs, such as the liver, even if the amplitudes will normally be lower than for the lungs. The motion will result in that parts of the treatment plan will be delivered to a different patient geometry than it was planned for. When the plan is delivered on a similar time scale as the variation in the patient geometry, large deviations between the planned and delivered dose can result. This is referred to as the interplay effect.

The interplay effect is a problem in all types of radiotherapy, but in particular in ion treatments delivered by pencil beam scanning, in which a beam is used to scan the tumour volume layer by layer with particles of different energy until the whole tumour has been covered.

Attempts to reduce interplay effects include gating techniques, to deliver the treatment in a specific part of the motion cycle, for example at the start of inspiration. This means that the time needed for delivering a fraction will increase significantly, since the radiation can only be delivered at a limited portion of each period. Motion mitigation techniques are also used, in which the patient's motion is restricted. This method will usually lead to discomfort for the patient, in particular if lung movement is restricted. To some extent controlling the patient's breathing cycle by means of breath coaching may reduce the problems. In ion pencil beam scanning, repainting strategies are used, in which the beam is delivered multiple times to get a statistical smearing effect over the motion cycle. This method increases the time of delivering a fraction significantly, since the delivery time of each energy layer scales by the number of paintings of that specific layer. Attempts have also been made with beam tracking, involving continuous tracking of the target and adjusting the beam to the target's actual position in real time. This method is promising, but it will probably take several years before it reaches clinical practice, due to current technical limitations. Moreover, there will inevitably be some residual uncertainty regarding the exact position of the target.

Robust optimization is already used to handle range and setup uncertainties as well as prompt delivery of the full plan to each of the phases in a 4DCT data set. Heath, Unkelbach and Oelfke: Incorporating uncertainties in respiratory motion into 4D treatment plan optimization, Medical Physics 36, 3059 (2009); doi 10.1118/1.3148582 discloses a method of accounting for respiratory motion uncertainties, in which the breathing cycle is divided into intervals based on a 4DCT image set. The motion trajectory for each moving voxel is determined and the time spent in each interval is calculated. The resulting dose distribution is based on the assumption that the whole plan will be delivered to each of the intervals, weighted by the time spent in the interval. However, in the prior art the distribution of the full plan over the different phases in the motion cycle is not taken into account.

SUMMARY OF THE INVENTION

It is therefore an aim of the invention to provide a reliable method of ensuring that the objectives of the treatment plan are fulfilled even if the target moves during a fraction. The invention strives towards reducing or discarding interplay effects caused by the patient's movements during a treatment fraction.

The invention relates to a method of optimizing a radiotherapy treatment plan for delivering radiation to a patient's body in at least one session, including the following steps:
  obtaining an initial radiotherapy treatment plan,
  obtaining a composite objective function, said composite objective function being based on at least one clinical goal for at least one region of the patient's body,
  selecting at least a first scenario for at least one variable that may change during one session, in such a way as to affect the dose delivery to the at least one region,
  calculating a dose distribution for the one session for the at least one scenario,
  performing robust optimization of the treatment plan based on the calculated dose distributions.

According to the invention a robust optimization technique is applied during the treatment planning. The robust optimization takes into account at least one factor that will vary so much as to affect the dose delivery in the time period needed for delivering a treatment fraction, ensuring that the dose delivery will meet the clinical goals regardless of which one of a number of possible scenarios regarding the factor or factors really applies during the session. Such factors typically include properties of the cyclic movement, such as its period, amplitude and shape, the phase of the cycle in which the treatment starts and the time structure of the delivery itself. The result is a treatment plan that is robust with respect to the interplay effect.

In a preferred embodiment, the at least one variable includes at least one of the following:
- a period and/or an amplitude and/or a shape of the movement of the at least one region,
- a position of the at least one region of the patient at the start of a treatment session,
- the time structure of the delivery of radiation to the patient.

In many cases, the patient movement will be a cyclic movement. In such cases, the method preferably includes defining a number of phases in a period of the cyclic movement. The position of the at least one region of the patient will preferably relate to a specific phase among the number of phases, in which the radiotherapy session is scheduled to begin.

The inventive method is designed for taking into account intra-fractional changes, that is, changes that occur during one single fraction. Over the course of the radiotherapy treatment this method may be combined with robust optimization with respect to inter-fractional changes (e.g. tumour shrinkage or growth). Robust optimization may also be performed with respect to systematic errors, such as errors in the patient setup during image acquisition or in the conversion from CT numbers to densities and/or stopping power ratios.

The radiotherapy treatment may also be adaptive, meaning that the result of the therapy after a number of sessions is evaluated and the plan is adapted on the basis of the evaluation before a subsequent session. The evaluation may take into account the actual accumulated dose, movements of organs or regions within the patient, changes in size of the target and/or other organs within the patient, etc.

Preferably the step of selecting at least one scenario comprises selecting at least two different scenarios. In this case the method preferably also includes the steps of
- defining a nominal value for the at least one variable and using the nominal value for a first scenario, and
- defining a second value different from the nominal value for the at least one variable and using the second value for a second scenario.

In order to account for variations around a nominal value, the method may comprise selecting at least three scenarios and also comprise the steps of
- defining a third value different from the nominal value the difference between the third value and the nominal value having the opposite sign of the difference between the second value and the nominal value, and using the third value for a third scenario.

The total number of scenarios to be defined may be chosen freely. Typically there will be a trade-off between the need to cover a sufficient number of relevant scenarios and the interest of keeping the computational times at an acceptable level.

The at least one target dose value typically relates to at least a minimum dose value for a first region of the patient's body, to ensure that the tumour receives a sufficient radiation dose. Often a maximum dose value for a second region of the patient's body will also be set, to limit the dose delivered to one or more critical organs. The target dose value may set a minimum or maximum for the entire region or set a more complex goal, for example that at least a certain percentage of the region should receive at least a minimum dose value.

The invention also relates to a computer program product comprising computer readable code means which, when run in a computer will cause the computer to perform the method according to any one of the preceding claims. As is common in the art, the computer program product is typically stored on a carrier, which may be any type of data carrier.

The invention also relates to a computer system for performing dose calculations for radiotherapy, the computer system comprising processing means and having a memory having stored therein a computer program product according to the above in such a way that the computer program product, when executed, will control the processing means. The computer preferably also comprises data memory for storing information to be used in the optimization procedure, such as a set of 4DCT scans of the patient and an initial treatment plan and/or clinical goals for the treatment. The processing means may additionally be arranged to perform the image registration between the images in the 4DCT scan set.

BRIEF DESCRIPTION OF THE DRAWINGS

The invention will be disclosed in more detail in the following, with reference to the appended drawings, in which.

DETAILED DESCRIPTION OF PREFERRED EMBODIMENTS

Figures 1A, 1B:
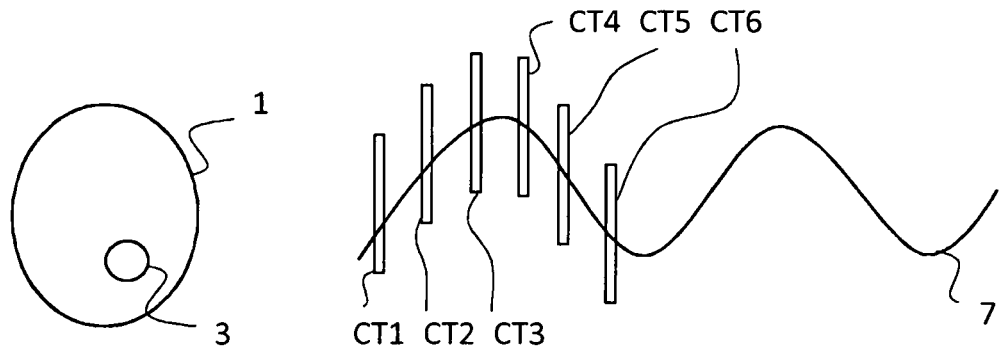
FIGS. 1a and 1b show an organ with a tumour and the distribution of scans in a 4DCT scan of the organ relative to the motion cycle.

FIG. 1a illustrates schematically an organ, in this case a lung 1, with a tumour 3 that is to be treated with radiotherapy. FIG. 1b illustrates two periods of the breathing cycle as a near sine curve 7. The sine curve is often a good approximation of a cyclic movement, but more complex cycles, and even non-cyclic movements, may also be considered. According to preferred embodiments a 4DCT scan is taken. This means that CT scans CT1, CT2, CT3, CT4, CT5, CT6 are obtained of the lung at different points in time during a breathing cycle, to determine the position of the tumour at the different points in time. A higher or lower number of CT scans may be used, and the scans are preferably but not necessarily obtained during one period of the cycle. Also, the scans may be obtained by CT imaging of the patient in combination with an approximation method. For example, additional scans may be generated by interpolation between two of the CT scans or by extrapolation from one of the CT scans. This will increase the resolution of the movement cycle by providing information related to more phases within the cycle.

In particular three different factors will influence the dose in each point: The phase of the cyclic movement in which the treatment starts, the position of the regions of interest such as the target and the healthy organs, and variations in the time structure of the actual dose delivery.

The different phases of the cyclic movement correspond to the different scans CT1-CT6 as shown in FIG. 1b. Each scan determines the position of the regions of interest at a specific time, and combined together the scans give information on the direction in which the regions will move. The outcome of the delivery is dependent on which phase the treatment starts in, since this determines which patient anatomy the different parts of the treatment plan are delivered on.

The position of the target depends on the cycle of movement, so changes in the cycle of movement will affect the dose and should therefore be taken into account. The cycle of movement may vary over the time of the fraction delivery. For example, both the period, the amplitude, and the shape of the breathing cycle may change if the patient coughs or becomes more stressed or more relaxed during the fraction delivery.

Variations in the time structure of the dose delivery will affect how the dose is distributed over the phases. In combination with the patient's movement, this means that the region where the beam will hit at any given point in time cannot be exactly known. Therefore, the optimization model should take into account possible variations in the delivery time structure of the treatment plan.

These three factors make it difficult to predict exactly in which part of the patient's anatomy the dose will be delivered. Therefore, they should be taken into account when optimizing the treatment. For the inventive method, different possible scenarios are defined, each scenario defining a combination of values for the variables discussed above.

Cyclic movements may also occur in other organs, such as the liver, but normally with lower amplitudes than the movement of the lungs. Such movements may also be considered according to the invention in the same way as described above. Moreover, non-cyclic movement can also be considered according to the invention, for example as described above but with the length of the cycle extending over the entire fraction.

Figures 2A, 2B, 2C:
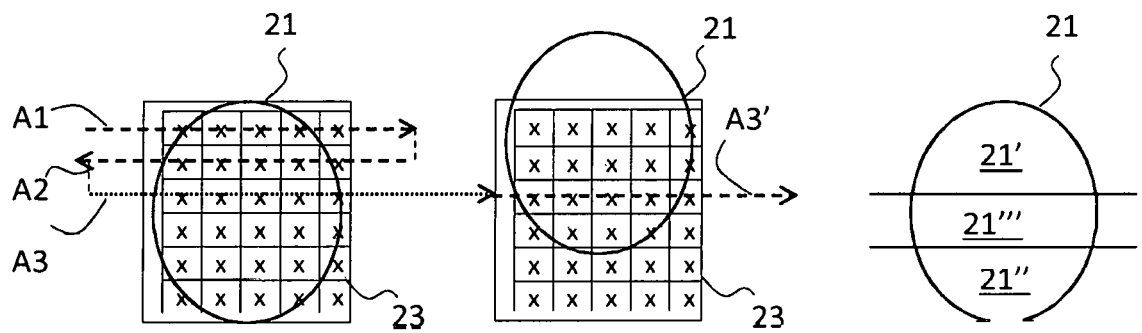
FIGS. 2a and 2b illustrate the dose delivery to a moving target.
FIG. 2c illustrates the resulting dose delivery in the target.

FIGS. 2a and 2b illustrate the dose delivery to an area of a patient using pencil beam scanning. For illustration purposes a tumour is shown schematically in each of FIGS. 2a and 2b as an ellipse 21, displaced upwards in FIG. 2b compared to FIG. 2a. The displacement may be caused, for example, by the patient inhaling. A 5×6 matrix 23 of spots within the tumour is indicated by an x for each spot. FIG. 2a is assumed to be the reference image. Dashed arrows A1, A2 and A3 indicate the sequence of pencil beam delivery: In this example, the beam is first scanned across the uppermost row of spots, then returns across the next row below and again in the first direction across the third row from the top. As will be understood this continues through all the rows of the matrix. If, during the time used to scan the two uppermost rows, the tumour has moved to the position shown in FIG. 2b, the beam aimed at the third row from the top will hit a lower portion of the tumour than originally intended. In this simple example, this means that the portion of the tumour that originally corresponded to the third and fourth rows of the matrix will not receive any radiation. FIG. 2c shows the tumour 21 after the dose delivery. In this example, the uppermost area 21' was hit by the pencil beam scanning its first two rows, as shown in FIG. 2a. Because the tumour moved, the third and fourth row scanned by the pencil beam hit the tumour in the lowermost area 21" indicated in FIG. 2c. The centre area 21''' between the uppermost 21' and the lowermost 21" area did not receive any dose in this example.

According to the invention, a robust optimization is performed to ensure that all organs or regions within the patient receive an appropriate dose even when the factors mentioned above vary. For the inventive method a number of scenarios are defined, each scenario being based on assumptions about the varying factors. Moreover, a composite objective function is defined, comprising a number of constituent functions, including dose targets for the different regions of interest in the patient and reflecting how well the goals of the treatment are fulfilled. For some regions, such as a tumour, a constituent function of the composite objective should relate to a minimum dose, whereas for healthy regions, a constituent of the composite objective should relate to a maximum dose to avoid damaging critical organs. The constituent functions could, for example, be based on a sum of deviations from the minimum and maximum dose values, or quantify the biological effects of the dose distribution within the different regions using a biological model. The robust optimization evaluates the dose distribution resulting under each considered scenario and updates the treatment plan iteratively in order to improve upon the totality of these scenarios with respect to the composite objective function.

Different measures of improvement can be used. For example, the composite objective value could be evaluated under all scenarios, and the optimization could aim to make the worst scenario value as beneficial as possible. It should be understood that the scenario that results in the worst objective value will typically change as the treatment plan changes. Another measure is the average or expected composite objective value over the scenario doses. In yet another measure, worst case dose distributions are defined, which specify the worst dose that each region of the patient, considered independently, could receive over the scenarios. For regions within the target, the minimum dose over the scenarios is typically considered to be the worst case dose. To avoid hot spots, the maximum dose could be considered in addition to the minimum dose for the target. For regions within healthy structures, the maximum dose over the scenarios is typically considered to be the worst case dose. The composite objective is then evaluated on the worst case dose distributions, and the optimization is aimed at making these dose distributions as beneficial as possible. There are many variations of these measures, as will be well known to the skilled person familiar with robust optimization. Naturally, objective constituents that are only evaluated with respect to one specific scenario (for example, the nominal scenario) could be added to the composite objective function. Moreover, robust and scenario-specific constraints could be added to the robust optimization.

It would also be possible to use a non-robust objective function with robust constraints. In this case the composite objective, or the individual constituents of the composite objective, might be set as constraints.

The delivery time structure of the plan will change during the optimization, because the optimization algorithm will alter the fluence in each iteration. In intensity-modulated radiation therapy (IMRT) and volumetric modulated arc therapy (VMAT) this is because the segment weights will change, and in intensity modulated particle therapy (IMPT) the spot weights will be changed. The weights will in turn determine the time needed for delivery of each segment or spot. Also, in IMPT, spot filtering is used, where spots below and above a certain monitor output (MU) value will be removed, and the spot order may also be subject to sorting, which will change the spot map and therefore affect the delivery time. To take this effect into account, the delivery time must be updated during the optimization, either in each iteration or in a transition after a number of iterations.

Figure 3:
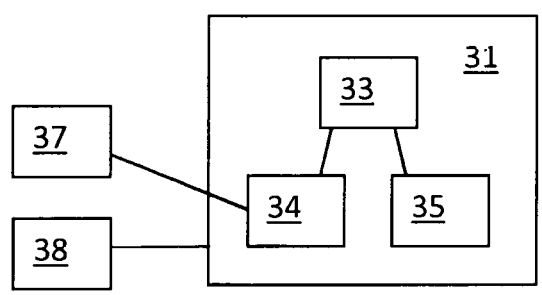
FIG. 3 is a schematic representation of a computer system in which the inventive method may be performed.

FIG. 3 is a schematic representation of a computer system in which the inventive method may be performed. A computer 31 comprises a processor 33, a data memory 34 and a program memory 35. The data memory 34 is arranged to receive from a CT imager 37 a set of CT scans of the relevant area of the patient taken over time to form a 4DCT scan. The CT scans are not necessarily received directly from the CT imager 37; they may alternatively be received from some other unit by any known communication method. Preferably, a user input means 38 is also present, in the form of a keyboard, a mouse, a joystick, voice recognition means or any other available user input means.

A treatment plan is found in the data memory 34. The treatment plan may be generated in the computer 31, or received from another storage means in any way known in the art.

The data memory 34 also holds one or more different scenarios as discussed above, to be used in the robust optimization procedure. These scenarios may be entered by means of the user input means 38 or other input means, or generated in the computer 31. The values may be based on values obtained from the CT scans, the treatment plan and/or other data. For example, one of the CT scans may be selected, manually or automatically, as the reference scan. The data memory 34 also holds information related to the composite objective function as will be discussed in more detail below.

As will be understood, the data memory 34 is only shown schematically. There may be several data memory units, each holding one or more different types of data, for example, one data memory for the treatment plan, one for the CT scans, etc. . . .

Figure 4:
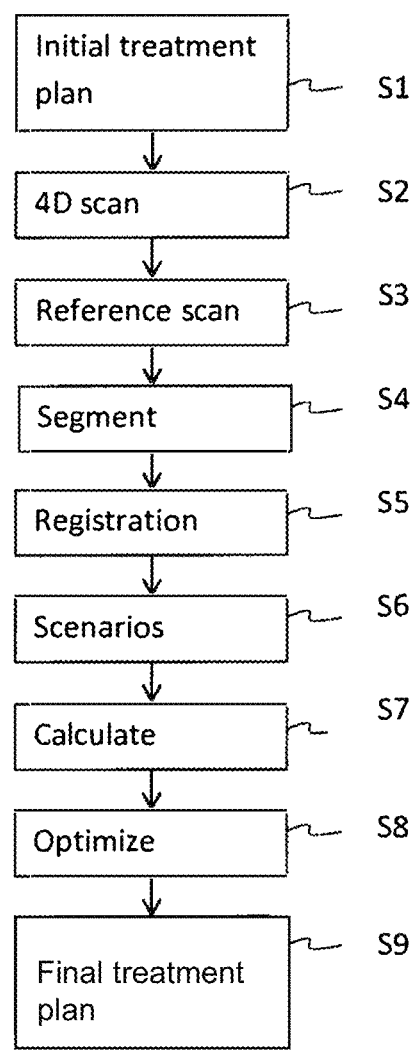
FIG. 4 is a flow chart of a method according to an embodiment of the invention.

The program memory 35 holds a computer program arranged to control the processor to perform the optimization as defined in FIG. 4. It will be understood that not all of the steps of the method of FIG. 4 are necessarily performed in the computer 31.

FIG. 4 is a flow chart of a method according to the invention.

In step S1 an initial treatment plan is obtained and a composite objective function is obtained based on the clinical goals of the treatment. The initial treatment plan comprises a partial treatment plan, including for example radiation angles. Other parameters needed to produce the final treatment plan will be calculated during the robust optimization. The initial plan may also comprise preliminary parameter values for the other parameters, to be adjusted during the optimization process. These other parameters typically include plan parameters such as the spot or segment weights. The clinical goals specify limits in terms of maximum and minimum doses for the different regions of the treated area and may be determined in any way known in the art. The actual configuration of the initial treatment plan is not part of the method according to the invention.

In step S2 a 4DCT scan of the relevant area of the patient is obtained. This involves obtaining a number of scans taken at different phases in the cycle. In step S3 a reference scan is selected, typically one of the scans obtained in step S2.

In step S4 each of the images is segmented to define the important structures in the patient's anatomy, such as the tumour and healthy organs.

In step S5, deformable registration is performed between each of the 4DCT scans and the reference scan, to obtain for each scan a displacement field representative of a relationship between the respective scan and the reference scan. It is worth noticing that the order between S4 and S5 is not strict, which means that sometimes it is preferred to perform S5 before S4.

In step S6 a number of different scenarios are defined, each scenario defining a value for one the variables above, or values for a combination of two or more of the variables. For example a certain phase of the cycle, say corresponding to the scan CT4, may be selected as a starting point, together with the average period and amplitude of the breathing cycle over a number of periods. Another scenario may involve the same or a different phase of the cycle, with a somewhat different period and/or amplitude.

In step S6 the different scenarios may advantageously be selected in such a way that a certain deviation on both sides of a nominal value is covered for each of the variables. This means that if a certain period of the cycle is assumed as the nominal value, there should be another scenario based on a somewhat longer period, and one based on a somewhat shorter period than the nominal period. The number of scenarios will vary depending on the complexity of the situation. The number of scenarios needed can also be reduced by combining this method with other methods, such as gating, as will be discussed in more detail below.

Each of the steps S3, S4, S5 and S6 may be performed automatically or by user input in the computer 31. They may also be performed in a different computer and the resulting segmented images, reference scan selection and/or scenarios, respectively, may be input to the computer 31.

In step S7 the resulting dose distribution is calculated for each of the scenarios. This involves adding together the dose distributed over all the phases (corresponding to the CT images in FIG. 1*b*) for all segments or spots. For each phase the dose distribution is determined and the resulting dose in the reference image is determined by means of dose deformation using the deformable registration between the respective CT scan and the reference image. This is necessary since the same segment or spot in the plan will be located in different positions in each of the CT scans CT1, . . . , CT6. For the CT scan selected as the reference image, of course no registration is required. The summed dose for each of the scenarios serves as an input to the robust optimization.

In step S8 the objective functions for the calculated resulting dose distributions for the scenarios are evaluated and robust optimization is performed. This involves optimizing the treatment plan with respect to all the objective functions for the different calculated dose distributions. The treatment plan is adjusted to minimize the objective functions to ensure that treatment according to the treatment plan will produce an acceptable result in the patient in all of the possible scenarios.

In step S9 the final treatment plan is calculated as a complete treatment plan to be used in radiotherapy treatment of the patient.

Although the invention is described above in relation to a cyclic patient movement, caused by the breathing cycle, it may also be used to consider other types of movement, such as a substantially linear movement, or a movement that has a longer period than the fraction delivery time. For example, it may be assumed that the urinary bladder will either be constant in size or increase during a fraction, so that any organ close to it will either not be affected, or will move in substantially one direction during the fraction but the movement will not be cyclic.

The accuracy and efficiency of the inventive method can be increased by combining it with other methods for controlling the dose delivery. It is particularly advantageous to combine the method with gating, to determine that the plan will be delivered in one or several particular phases of the cycle, for example at the beginning of inspiration, corresponding to CT scan CT1 in FIG. 1*b*. To determine the correct phase for gating, different methods can be used. It is for example possible to track the chest movements, or other relevant movement, of the patient. This may be done by means of a simple strap registering the position of the patient's chest to determine when it is at its highest and lowest position, respectively. It may also be done by imaging the patient or in any other suitable way. The most precise method would be to combine the robust optimization with tumour tracking in which the position of the tumour is determined, for example, by means of a laser position means, a sensor attached to the patient, or a camera.

As an alternative to this, the method may be combined with repainting techniques as discussed in the background section, that is, letting the beam scan the target several times, delivering only part of the fraction in each scan. In each of the scans, the starting point of the delivery will be different, removing parts of the interplay effects.

The robust optimization method of the invention may also be combined with techniques for restricting the movement in terms of amplitude or period variations. For example restricting means may be applied to keep the patient's chest below a certain limit. Also breathing may be controlled to achieve a reproducible breathing cycle using breath coaching. These methods will limit the number of potential scenarios that have to be taken into account, enabling more precise calculations with less data than by applying a robust optimization method on its own.

Another method to reduce the number of scenarios would be to smear out spot or segment weights over time and redistribute them over a sequence of images. The smearing distribution should be selected to model the nature of the uncertainty of the anatomy motion. This would then limit the number of scenarios needed to take into account variations in the patient movement and changes in the delivery time structure.

Assuming that there are 10 phases in a breathing cycle and that three cycles should be selected to account for the reference cycle and one cycle that is longer and one that is shorter than the reference cycle, respectively, and two different scenarios for the time structure of delivery, this amounts to 60 different scenarios. By keeping one of the variables constant, the number of scenarios can be reduced, for example by determining the phase in which the treatment will start so that all 10 phases do not have to be considered as possible starting points.

After delivery of a dose fraction, it may be known which scenario applied and the actual dose distribution in the patient can be determined and compensated for in subsequent fractions. This is however, not part of the invention and will not be discussed in any detail here.

The invention claimed is:

1. A method of optimizing a radiotherapy treatment plan for delivering radiation to a patient's body in at least one session, wherein a delivery of radiation has a time structure, the method including the following steps:
   a. obtaining an initial radiotherapy treatment plan,
   b. obtaining a composite objective function, said composite objective function being based on at least one clinical goal for at least one region of the patient's body,
   c. selecting a first scenario including the time structure of the delivery of radiation and at least one variable related to a position of the at least one region of the patient's body, wherein the position may change during the at least one session in such a way as to affect a dose delivery to the at least one region of the patient's body,
   d. calculating a dose distribution for the at least one session for the first scenario, and
   e. performing robust optimization of the initial radiotherapy treatment plan based on the calculated dose distribution.

2. The method according to claim 1, further comprising selecting a second scenario different from the first scenario and
   f. defining a nominal value for the at least one variable and using the nominal value for the first scenario, and
   g. defining a second value different from the nominal value for the at least one variable and using the second value for the second scenario.

3. The method according to claim 2, further comprising the step of selecting a third scenario different from the first and second scenarios, and
   h. defining a third value different from the nominal value, a difference between the third value and the nominal value having an opposite sign of the difference between the second value and the nominal value and using the third value for the third scenario.

4. The method according to claim 1, wherein the at least one variable includes at least one of the following:
   a period, an amplitude, or a shape of a movement of the at least one region of the patient's body, or
   a position of the at least one region of the patient at a start of a treatment session.

5. The method according to claim 1, wherein patient movement is a cyclic movement, the method including defining a number of phases in a period of the cyclic movement.

6. The method according to claim 5, wherein the at least one variable includes at least one of the following:
   a period, an amplitude, or a shape of a movement of the at least one region of the patient's body, or
   a phase among the number of phases in which a radiotherapy session begins.

7. The method according to claim 1, wherein the composite objective function comprises a minimum dose value for a first region among the at least one region of the patient's body and a maximum dose value for a second region among the at least one region of the patient's body.

8. The method according to claim 1, further comprising tracking the at least one region of the patient's body by motion detection means and using a result of the tracking as input data for calculating the dose distribution.

9. The method according to claim 1, further comprising performing robust optimization with respect to systematic errors.

10. The method according to claim 1, wherein the delivery of radiation is performed in the at least one session and a second session, further comprising performing robust optimization with respect to inter-fractional changes.

11. The method according to claim 1, wherein the delivery of radiation is performed in the at least one session and a second session, further comprising evaluating dose delivery after the at least one session and adapting a final radiotherapy treatment plan before the second session on the basis of the evaluation.

12. A computer program product comprising non-transitory computer readable code means which, when run in a computer will cause the computer to perform the method according to claim 1.

13. The computer program product of claim 12, stored on a carrier.

14. A computer system for performing dose calculations for radiotherapy, the system comprising processing means, said computer system having a program memory having stored therein a computer program product according to claim 12 in such a way that the computer program product, when executed, will control the processing means.

15. The computer system according to claim 14, further comprising a data memory arranged to hold data to be used by the processing means when performing the robust optimization.

16. The computer system according to claim 15, wherein data to be used by the processing means when performing the robust optimization comprises image data related to the patient, the initial radiotherapy treatment plan, or information related to the first scenario.

* * * * *